United States Patent [19]

Naito et al.

[11] Patent Number: 5,109,131

[45] Date of Patent: Apr. 28, 1992

[54] METHOD FOR PRODUCTION OF T-BUTYL 3-OXOBUTYRATES AND THEIR USE

[75] Inventors: Kenzo Naito, Kyoto; Yukio Ishibashi, Osaka; Haruo Shinbo, Hyogo, all of Japan

[73] Assignee: Takeda Chemical Industries, Ltd., Osaka, Japan

[21] Appl. No.: 295,516

[22] Filed: Jan. 11, 1989

[30] Foreign Application Priority Data

Jan. 14, 1988 [JP] Japan ................................. 63-6133
Jun. 29, 1988 [JP] Japan ............................. 63-161984

[51] Int. Cl.$^5$ .......................................... C07D 501/36
[52] U.S. Cl. ................................... 540/227; 540/222; 540/225
[58] Field of Search ............... 540/228, 225, 226, 221, 540/222, 227

[56] References Cited

U.S. PATENT DOCUMENTS 4,399,132 8/1983 Curran et al. ...................... 424/246

FOREIGN PATENT DOCUMENTS 2012276 7/1979 United Kingdom .

OTHER PUBLICATIONS

Sven-Olov Lawesson et al., "Acetoacetic Acid, Tert-butyl Ester", Organic Syntheses, vol. 42, (1962) pp. 28–29.

Stephen R. Wilson et al., "The Ester Enolate Carroll Rearrangement", J. Org. Chem., vol. 49, (1984) pp. 722–725.

*Primary Examiner*—Nicholas S. Rizzo
*Attorney, Agent, or Firm*—Wegner, Cantor, Mueller & Player

[57] ABSTRACT

Disclosed are an advantageous method of industrial production of tert-butyl 3-oxobutylate, which is a useful intermediate for synthesis, characterized by reacting tert-butyl alcohol with diketene in the presence of 4-(tertiary amino) pyridine, and an industrially advantageous method of producing cephalosporin compounds or pharmaceutically acceptable salts thereof, using tert-butyl 3-oxobutylate as an intermediate.

9 Claims, No Drawings

METHOD FOR PRODUCTION OF T-BUTYL 3-OXOBUTYRATES AND THEIR USE

The present invention relates to an advantageous method of industrial production of tert-butyl 3-oxobutyrate useful as an intermediate for synthesis, especially as an intermediate for synthesizing cephalosporin compounds, and also relates to an industrially advantageous method of producing a cephalosporin compound using tert-butyl 3-oxobutyrate as an intermediate.

tert-Butyl 3-oxobutyrate is an important intermediate for synthesis in various industrial fields of, for example, agricultural chemicals, medicines, dyestuff or the like.

The use as intermediate for synthesis is described in, for example, "Chemical Reviews" 86, pp.248 to 249(1986), "Organic Synthesis Collective" 5, pp.155 to 157(1962), etc. And, tert-butyl 3-oxobutyrate is useful, in the pharmaceutical industry, as an important synthetic intermediate in the production of aminothiazole cephalosporins represented by, for example, cefmenoxime. Several kinds of aminothiazole cephalosporins have already been put on the market as antibiotics having a remarkably broad antimicrobial spectrum and have been widely used clinically. The chemical structures, pharmacological activities and production methods are described in "Angewandte Chemie: International Edition in English" 24, pp.180 to 202(1985), "Journal of Antibiotics" 38, pp. 1738 to 1751(1985), etc. In these methods of producing aminothiazole cephalosporins, it is tert-butyl 3-oxobutyrate that is used as the synthetic intermediate of the aminothiazole moiety. Methods of producing aminothiazole cephalosporins using tert-butyl 3-oxobutyrate as the synthetic intermediate are described in, for example, "Journal of Antibiotics" 38, p.p.1738 to 1751(1985), U.S. Pat. No. 4107380, U.S. Pat. No. 4191673, etc.

And, tert-butyl 3-oxobutyrate is conventionally prepared by a process which comprises allowing tert-butyl alcohol to react with diketene in the presence of sodium acetate ["Organic Synthesis" 42 p.p.28 to 29, 1962)], etc.

In conventional processes of producing tert-butyl 3-oxobutyrate, however, there are such drawbacks as set forth below:

(1) the reaction is necessarily conducted at relatively high temperatures(110° to 115° C.)(resulting in intense coloration of the reaction mixture, giving dehydroacetic acid as a by-product and, in most cases, necessitating a refining process of, e.g. distillation, before feeding the product to the subsequent reaction step), or (2) the yield is not always high.

Therefore, the conventional methods cannot be considered as industrially advantageous ones.

The present inventors conducted various studies on industrially advantageous methods of producing tert-butyl 3-oxobutyrate, and as a result, found that tert-butyl 3-oxobutyrate can be obtained in a high purity and a high yield unexpectedly under such mild conditions as requiring no heating or cooling from outside by allowing tertiary butyl alcohol to react with diketene in the presence of 4-(tertiary amino)pyridine and that the thus-obtained reaction mixture of tert-butyl 3-oxobutyrate can be used as the material for the subsequent process without purification. On the basis of these findings, the present invention was accomplished.

Namely, the present invention relates to a method of producing tert-butyl 3-oxobutyrate, which is characterized by allowing tertiary butyl alcohol to react with diketene in the presence of 4-(tertiary amino)pyridine.

As the 4-(tertiary amino)pyridine, use is made of pyridines having tertiary amino groups substituted at the 4-position. As such pyridines, use is made of, among others, compounds represented by the formula:

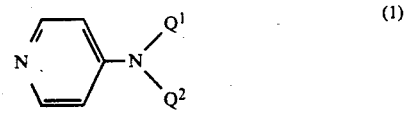

wherein $Q^1$ and $Q^2$ independently stand for an alkyl group or they are combined together with the adjacent nitrogen atom to form a cyclic amino group. In the formula(I), as the alkyl groups shown by $Q^1$ or $Q^2$, use is made of a lower alkyl group having 1 to 6 carbon atoms such as methyl, ethyl, propyl, isopropyl, butyl, etc. And, as the cyclic amino group shown by $Q^1$ and $Q^2$ combinedly together with the adjacent nitrogen atom, use is made of, for example, a piperidino, 4-methyl piperidino or pyrrolidino group. Specific examples of the pyridines(I) include 4-(dimethylamino)pyridine, 4-(diethylamino)pyridine, 4-(di-n-propylamino)pyridine, 4-(diisopropylamino)pyridine, 4-(N-methyl-N-ethylamino)-pyridine, 4-(N-ethyl-N-n-propylamino)-pyridine, 4-pyrrolidinopyridine, 4-(4-methylpyrrolidino)pyridine, 4-piperidinopyridine, etc. These 4-(tertiary amino)pyridines can be recovered after finishing this reaction and can be used repeatedly. Examples of preferable 4-(tertiary amino)pyridine include 4-(di-$C_{1-3}$ alkylamino)pyridine such as 4-(dimethylamino)pyridine. 4-(tertiary amino)pyridine can accelerate the reaction in a catalytic amount, i.e., usually 0.001 to 1 mol. relative to 1 mol. of tert-butyl alcohol, preferably 0.001 to 0.02 mol.

This reaction is conducted usually in the absence of solvent, but it may be carried out in a non-protonic organic solvent which does not give undesirable effects upon the reaction. Examples of such non-protonic organic solvents include nitriles such as acetonitrile, ethers such as tetrahydrofuran, 1,2-dimethoxyethane, dioxane or diethylether, halogenated hydrocarbons such as methylene chloride, chloroform or carbon tetrachloride, esters such as ethyl acetate, butyl acetate, amides such as N, N-dimethylformamide or N,N-dimethylacetamide, hydrocarbons such as benzene, toluene, xylene, hexane or pentane, or a mixture of them. The volume of such non-protonic organic solvent to be used is in the range of from 0.2 to 20 l relative to 1 mol. of tert-butyl alcohol, preferably 1 to 5 l. The amount of diketene to be used is usually 1 mol. relative to 1 mol. of tertiary butyl alcohol, but it may be in the range of from 0.5 to 1.5 mol. This reaction can also be carried out by adding diketene dropwise to a mixture of tert-butyl alcohol and 4-(tertiary amino)pyridine, and, in this case, unexpectedly, the object of this reaction can be attained even in the absence of solvent. The reaction temperature usually ranges from 0° C. to 100° C., preferably from 25° C. to 80° C. Since the present reaction is exothermic, no heating is required at all for maintaining the above-mentioned temperature range. When the reaction temperature rises too high by the heat of the reaction, the reaction temperature can easily be adjusted within the range by using industrial cooling water or the like. And, it is not necessary at all to adjust the reaction temperature to 0° C. or lower by using a cooling agent such as liquid nitrogen, etc., which has so far been considered to be indispensable to prevent the polymerization of diketene per se. For maintaining such reaction temperature, it is preferable to add diketene dropwise. The time required for this dropwise addition usually ranges from 0.2 to 10 hours, preferably 0.3 to 3 hours, while the range is not specifically limited so long as the object can be attained. By adjusting the rate of dropwise addition of diketene, the reaction can be allowed to proceed without heating or cooling. The reaction time after completing the dropwise addition of diketene varies with the solvent then used, reaction temperature, etc., but it usually ranges from 0.2 to 5 hours, preferably from 0.3 to 2 hours.

The thus-obtained tert-butyl 3-oxobutyrate can be used as the material of the subsequent process in the state of the reaction mixture. Or, the reaction mixture can be used as the material of the subsequent process after isolation and purification by means of, for example, concentration, distillation, pH-change, solvent-extraction, chromatography, etc.

The thus-produced tert-butyl 3-oxobutyrate can be used for the production of cephalosporin compounds by the following reaction processes.

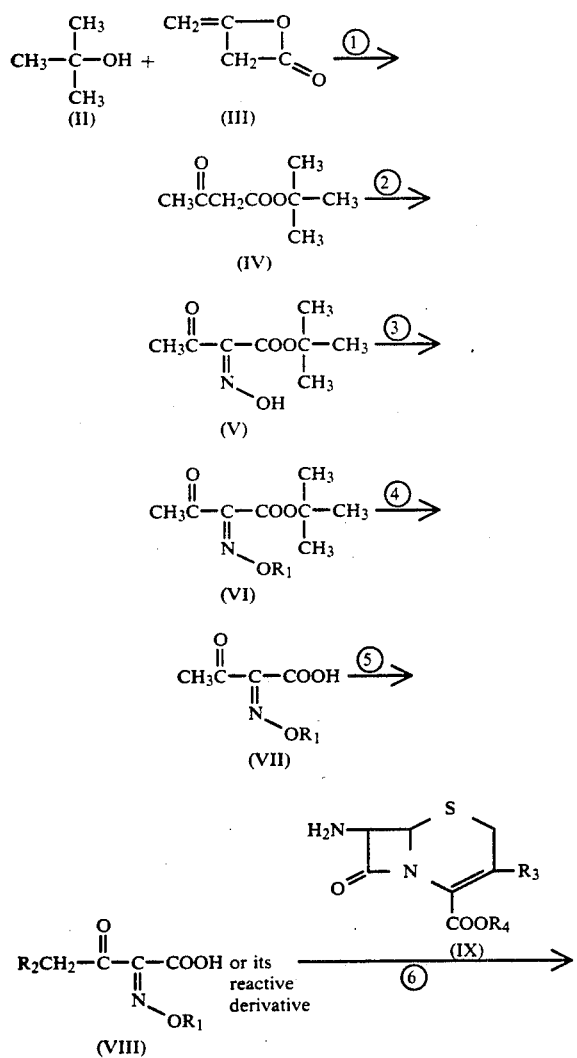

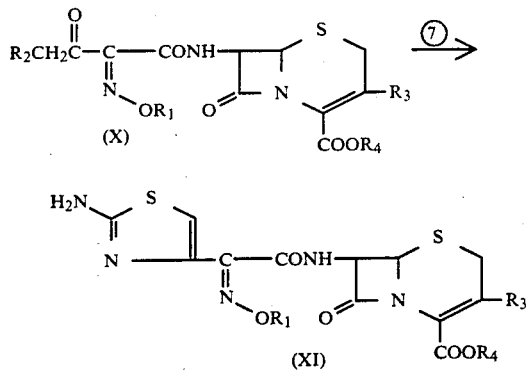

The process ① as explained above.

The process ② is carried out by allowing tert-butyl 3-oxobutyrate to react with a nitrosating agent. The agent is exemplified by nitrous acid, esters of nitrous acid such as methyl nitrite, ethyl nitrite, amyl nitrite, etc., nitrosyl halides such as nitrosyl chloride, etc. And, nitrous acid may be produced in the reaction system by allowing an alkali nitrite (e.g. sodium nitrite, etc.) to react with an acid (e.g. hydrochloric acid, acetic acid, etc.) This reaction is conducted usually in a solvent, and any solvent can be used unless it hampers the reaction. Practical examples of such solvent are dioxane, tetrahydrofuran, water, acetic acid or a mixture of these solvents.

The reaction can be carried out usually in the range of from $-20°$ C. to $50°$ C. The reaction may go to completion in 5 minutes to 24 hours, preferably in a short time (20 minutes to 10 hours). The reaction product (V) can be subjected to the subsequent reaction after isolation by a conventional means or without isolation.

The process ③ can be carried out by allowing the thus-produced compound (V) to react with an alkylating agent. Specific examples of the alkylating agent include dialkyl sulfates such as dimethyl sulfate, diethyl sulfate, etc., diazoalkanes such as diazomethane, diazoethane, etc., alkyl halides such as methyl iodide, ethyl iodide, etc. and alkyl esters of sulfonic acid such as a methyl ester of p-toluenesulfonic acid.

The reaction employing dialkyl sulfate, alkyl halide or alkyl ester of sulfonic acid is carried out usually in water, acetone, ethanol, ether, dimetylformamide or any other solvent which does not give any undesirable influence upon the reaction. This reaction is carried out preferably in the presence of an inorganic or organic base. The reaction temperature is not specifically limited, but the reaction is carried out, in most cases, in the range of from cooling to heating up to about the boiling point of the solvent then used. The reaction time is usually 0.1 to 40 hours, preferably 0.5 to 12 hours.

The reaction employing diazoalkane is carried out usually in a solvent such as ether, tetrahydrofuran, etc. The reaction temperature is not specifically restrictive, but, usually within the range of from cooling to room temperatures.

The starting compound (V) may be an alkali metal salt such as sodium, potassium, etc. at the hydroxyimino group. The alkyl group which may be substituted as represented by $R_1$ in the compounds (VI) to (VIII), (X) and (XI) produced according to this invention may be, for example, $C_{1-4}$ alkyl such as methyl, etc., or $C_{1-4}$ alkyl optionally substituted with carboxyl, a $C_{1-4}$ alkoxy-carbonyl or the like, for example, carboxymethyl, carboxypropyl, 1-carboxy-1-methylethyl, 1-tert-butoxycarbonyl-1-methylethyl, etc.

The process ④ is carried out by subjecting the thus-produced compound (VI) to de-esterification. The de-esterification is conveniently carried out by allowing the compound (VI) to react with hydrogen halide. As the hydrogen halide, use is made of, for example, hydrogen chloride, hydrogen bromide, etc. and, preferably hydrogen chloride.

This reaction is carried out preferably in an anhydrous organic solvent. As the organic solvent, any one which does not adversely affect the reaction can be used, for example, nitriles such as acetonitrile etc., ethers such as tetrahydrofuran, 1,2-dimethoxyethane, dioxane, diethyl ether, etc., halogenated hydrocarbons such as carbon tetrachloride, etc., esters such as ethyl acetate, butyl acetate, etc., amides such as N,N-dimethylformamide, N,N-dimethylacetamide, etc., hydrocarbons such as benzene, toluene, xylene, hexane, pentane, etc., or a mixture of these solvents, and, above all, halogenated hydrocarbons(especially chlorinated hydrocarbon such as methylene chloride) are often used as preferable ones. The volume of such organic solvent is usually 0.1 to 10 l relative to 1 mol. of the compound (VI), preferably 0.5 to 2 l. Presence of water in the reaction mixture accelerates occurrence of by-products, and, therefore, it is preferable to minimize the amount of water in the reaction mixture as far as possible. For that purpose, as the above-mentioned organic solvents, such containing as little water as possible, i.e. it is desirable to employ substantially anhydrous ones.

This reaction can be carried out conveniently by allowing the compound (VI) to react with hydrogen halide in an anhydrous organic solvent. More specifically, this reaction is usually carried out being catalyzed by hydrogen halide gas, which is blown into the compound (VI) in an anhydrous organic solvent, when desired under elevated pressure or while stirring. The reaction may also be effected by dissolving the hydrogen halide in advance in the anhydrous organic solvent employed, if desired under pressure or with stirring, and then adding the tert-butyl 2-substituted oxyimino-3-oxobutyrate to the thus-prepared solution. The hydrogen halide is used generally in an amount of 1 to 10 moles, preferably 1 to 6 moles, per mole of tert-butyl 2-substituted oxyimino-3-oxobutyrate, although said amount may vary depending on the organic solvent employed. When, in particular, an alkylene chloride, such as methylene chloride, which is preferred as the organic solvent, is used, the hydrogen halide is used generally in an amount of 1 to 3 moles, preferably 1.2 to 2 moles, per mole of tert-butyl 2-substituted oxyimino-3-oxobutyrate.

The reaction temperature is not critical. The only requirement is that the reaction can proceed at the temperature employed. Generally, however, the reaction is carried out at −50° C. to 80° C., preferably 0° C. to 30° C. The hydrogen halide is blown into the starting material-solvent mixture generally over a period of 0.5 to 20 hours, preferably 2 to 10 hours, although the period of hydrogen halide feeding should be varied depending on the reaction temperature, the solvent and the hydrogen halide quantity. Then, the reaction mixture is recommendably stirred or allowed to stand generally for 1 to 24 hours, preferably 2 to 15 hours. In case where the hydrogen halide is dissolved in advance in the solvent, for example, by blowing into the reaction system, it is preferable to stir usually for 1 to 40 hours, preferably 2 to 20 hours after the addition of the compound (VI), while varying with the reaction temperatures, solvents used, the amount of hydrogen halide used, etc.

The compound (VII) produced by the reaction can be subjected to the subsequent reaction as in the state of the reaction mixture or after isolation and purification by conventional means such as concentration, pH change, solvent extraction, crystallization, recrystallization, chromatography, etc.

The process ⑤ comprises subjecting the thus-produced compound (VII) to halogenation to obtain the compound (VIII).

As the halogenating agent for this halogenation, use is made of, for example, halogen (chlorine, bromine, iodine, etc.), halogenated sulfuryl (sulfuryl chloride, etc.), N-halogenosuccinimide (N-bromosuccinimide, N-chlorosuccinimide, etc.), 1,3-dibromo-5,5-dimethylhydantoin, etc., and, especially, bromine, sulfuryl chloride, N-bromosuccinimide, etc. are often used. These halogenating agents are used usually in an amount of 0.5 to 1.5 mol. relative to the compound (VII). This halogenation is carried out usually in a solvent. As the solvent, any one which does not affect the reaction adversely can be employed, as exemplified by hydrocarbons such as hexane, benzene, toluene, xylene, etc., ethers such as tetrahydrofuran, isopropyl ether, dioxane, diethyl ether, etc., halogenated hydrocarbons such as methylene chloride, chloroform, carbon tetrachloride, etc., esters such as ethyl acetate, etc., ketones such as acetone, etc., amides such as N,N-dimethylformamide, N,N-dimethylacetamide, etc. or a mixture thereof. Preferable solvents are exemplified by halogenated hydrocarbons such as methylene chloride, etc., ethers such as tetrahydrofuran, etc., etc. The reaction temperatures are not specifically limited so long as the desired halogenation proceeds, and, usually ranging from −50° C. to 80° C., preferably from −20° C. to 30° C. Anhydrous acid catalysts can also be employed, which are exemplified by inorganic acids such as hydrogen chloride, hydrogen bromide, sulfuric acid, phosphoric acid, dichlorophosphoric acid, etc., organic acids such as formic acid, acetic acid, p-toluenesulfonic acid, methanesulfonic acid, trifluoroacetic acid, etc., Lewis acids such as boron fluoride, aluminium chloride, titanium tetrachloride, etc., etc. A preferable anhydrous acid catalyst is exemplified by commercially available acetic acid solution of hydrogen bromide. And, in this halogenation, as the starting material, the compound (VII) produced by the process ④ can be employed as in the state of the reaction mixture. In this case, an excess portion of the hydrogen halide used in the process ④ can be employed as the anhydrous acid catalyst in this halogenation reaction. Therefore, it is advantageous from the viewpoint of industrial large scale production to carry out this halogenation succeeding the process ④. The reaction time varies with the solvents, halogenating agents, anhydrous acid catalysts, reaction temperatures and any other conditions then employed, and it is usually in the range of from 0.5 to 20 hours, preferably 1 to 6 hours.

Thus-obtained compound (VIII) may be used as the synthetic intermediate as in the state of the reaction mixture, or after isolation and purification by conventional means such as concentration, pH change, solvent extraction, crystallization, recrystallization, chromatography, etc. Typical examples of thus-obtained compound (VIII) are set forth as follows: (i) 4-chloro-2-methoxyimino-3-oxobutyric acid (ii) 4-bromo-2-methoxyimino-3-oxobutyric acid (iii) 4-iodo-2-methoxyimino-3-oxobutyric acid The process ⑥ comprises allowing the compound (VIII) or a reactive derivative thereof to react with the compound (IX) or a salt thereof to produce the compound (X) or a salt thereof. $R_2$ in the formulae (VIII) and (X) stands for a halogen atom such as chlorine, bromine, fluorine, iodine, etc., and usually chlorine and bromine are employed.

The substituent $R_3$ on the cephem ring in the formulae (IX) and (X) stands for hydrogen atom, $-CH_2R_5$ ($R_5$ stands for hydrogen atom or the residual group of a nucleophilic compound), halogen atom, an optionally substituted hyroxyl group, lower alkenyl group having 2 to 4 carbon atoms (e.g. vinyl group, 1-propenyl group, etc.), thiol group or amino group or

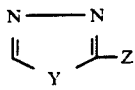

wherein Y stands for oxygen atom, sulfur atom or an optionally substituted imino group, Z stands for hydrogen atom or an optionally substituted hydroxyl group, amino group, thiol group or hydrocarbon group. $R_5$ stands for hydrogen or the residual group of a nucleophilic compound, and examples of the residual group $R_5$ include a hydroxyl group, mercapto group, a lower aliphatic acyloxy group having 2 to 4 carbon atoms which may optionally be substituted by oxo, carboxyl, $C_{1-4}$ alkoxycarbamoyl or the like, such as acetyloxy group, propionyloxy group, 3-oxobutyryloxy group, 3-carboxypropionyloxy group, 3-ethoxycarbamoylpropionyloxy group, 4-carboxybutyryloxy group, etc., an aromatic acyloxy group which may optionally be substituted by hydroxyl, carboxy, $C_{1-4}$ alkoxy-carbonylcarbamoyl, $C_{1-4}$ alkoxy-carbonylsulfamoyl or the like, such as mandelyloxy group, 2-carboxybenzoyloxy group, 2-(carboethoxycarbamoyl)benzoyloxy group, 2-(carboethoxysulfamoyl)benzoyloxy group, etc., carbamoyloxy group, cyano, azido, amino, carbamoylthio, thiocarbamoyloxy, carbamoyloxy group wherein the amino group is protected with the conventional protective group for amino (e.g. N-mono-, di- and trihalogenoacetylcarbamoyloxy group such as N-chloroacetylcarbamoyloxy group, N-dichloroacetylcarbamoyloxy group, N-trichloroacetylcarbamoyloxy group, etc., N-chlorosulfonylcarbamoyloxy group, N-trimethylsilylcarbamoyloxy group), and phenylglycyloxy group, or these residual groups of nucleophilic compounds may be further substituted with an alkyl group(e.g. $C_{1-3}$ lower alkyl group such as methyl, ethyl, propyl, etc.) or an acyl group (e.g. $C_{2-4}$ lower aliphatic acyl group such as acetyl, propionyl, butyryl, etc., or an aromatic acyl such as benzoyl, p-chlorobenzoyl, p-methylbenzoyl, mandeloyl, etc.), and, in this case, the number of substituents is usually 1 to 2. Or, the residual group $R_5$ may be a quaternary ammonium group, and it also stands for a heterocyclic group bonded through S, namely heterocyclic thio group. The heterocyclic thio group has a 5- or 6-membered ring containing 1 to 4 hetero-atoms selected from O, S or N, and the nitrogen atom may be in the form of oxide. As these heterocyclic groups, use is often made of, for example, pyridyl, N-oxidopyridyl, pyrimidyl, pyridazinyl, N-oxidopyridazinyl, pyrazolyl, imidazolyl, thiazolyl, 1,2,3-thiadiazolyl, 1,2,4-thiadiazolyl, 1,3,4-thiadiazolyl, 1,2,5-thiadiazolyl, oxazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2-tetrazolyl, etc. And, these heterocyclic thio groups may have on the heterocyclic ring substituent(s) including a $C_{1-3}$ lower alkyl group such as methyl, ethyl, propyl, etc., a $C_{1-3}$ lower alkoxy group such as methoxy, ethoxy, propoxy, etc., a halogen atom such as chlorine, bromine, etc., trihalogeno-substituted $C_{1-3}$ alkyl such as trifluoromethyl, trichloroethyl, etc., hydroxyl group, mercapto group, amino group, carboxyl group, carbamoyl group, a di-$C_{1-3}$ alkylamino-$C_{1-3}$ alkyl group such as dimethylaminoethyl, dimethylaminomethyl, etc., carboxymethyl group, etc. The number of these substituents is usually 1 to 2. As the quaternary ammonium group shown by $R_5$, use is often made of, for example, pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-(carboxylmethyl)pyridinium, 4-(hydroxymethyl)pyridinium, 4-(trifluoromethyl)-pyridinium, quinolinium, picolinium or lutidinium, etc. And, when $R_3$ stands for halogen atom, optionally substituted hydroxyl group, $C_{2-4}$ alkenyl group, thiol group or amino group, as the halogen atom, use is made of, for example, chlorine, bromine, etc. as mentioned above. The hydroxyl group, $C_{2-4}$ alkenyl group, thiol group or amino group may be respectively substituted. As the substituents, use is made of, for example, a hydrocarbon group e.g. alkyl (preferably $C_{1-4}$) such as methyl, ethyl, etc., aralkyl (preferably $C_{7-9}$) such as benzyl, etc., and $C_{6-10}$ aryl such as phenyl, etc., acyl group (preferably $C_{2-8}$) such as acetyl, benzoyl, etc. and so on, and these substituents may be further substituted with carboxyl group, sulfo group, hydroxyl group, etc. And, in the case of amino group, are included pyrrolidino, morpholino, thiomorpholino, etc. formed by linkage with the N-atom. Specific examples include hydroxyl group, methoxy group, ethoxy group, methylthio group, carboxymethylthio group, phenylthio group, amino group, dimethylamino group, ethylamino group, 2-dimethylaminoethyl group, chlorine, bromine, etc. And, when $R_3$ stands for

Y stands for oxygen atom, sulfur atom or an optionally substituted imino group. Examples of substituents of the optionally substituted imino group include a lower alkyl group (preferably having 1 to 3 carbon atoms) such as methyl, ethyl, etc., or a lower alkyl group (preferably having 1 to 4 carbon atoms) substituted with hydroxyl group, mercapto group, amino group, morpholino group, carboxyl group, sulfo group, carbamoyl group, alkoxycarbonyl group (preferably having 2 to 6 carbon atoms), lower alkylcarbamoyl group (preferably having 2 to 6 carbon atoms), alkoxy group (preferably 1 to 4 carbon atoms), alkylthio group (preferably 1 to 4 carbon atoms), alkylsulfonyl group (preferably 1 to 4 carbon atoms), acyloxy group (preferably 2 to 4 carbon atoms) or morpholinocarbonyl group, $C_{6-10}$ aryl group such as phenyl group, etc., $C_{7-10}$ aralkyl group such as benzyl group, etc., acyl group (preferably having 1 to 5 carbon atoms) such as acetyl group, propionyl group, benzoyl group, etc. Examples of the substituents of hydroxyl group, amino group, thiol group or hydrocarbon group [for example, alkyl groups (preferably having 1 to 4 carbon atoms) such as methyl, ethyl, propyl, isobutyl, tert-butyl, etc., $C_{7-10}$ aralkyl group such as benzyl, etc., $C_{6-10}$ aryl group such as phenyl, naphthyl, etc., etc.] shown by Z include lower alkyl, acyl group, aralkyl group, aryl group, etc. as described in the foregoing. These substituents may be further substituted with carboxyl group, sulfo group, hydroxyl group, etc. And, in the case of amino group, there may be included cases where pyrrolidino group, morpholino group, thiomorpholino group, etc. may be formed together with the N-atom.

Specific examples of

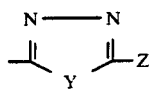

include 5-acetylamino-1,3,4-thiadiazol-2-yl, 5-amino1,3,4-thiadiazol-2-yl, 5-dimethylamino-1,3,4-thiadiazol2-yl, 5-methyl-1,3,4-thiadiazol-2-yl, 1,3,4-thiadiazol2-yl, 5-acetamido-1,3,4-triazol-2-yl, 5-acetamido-1,3,4-oxadiazol-2-yl, etc. The optionally esterified carboxyl group shown by $-COOR_4$ in the formulae (IX), (X), and (XI) means carboxyl group or its inorganic or organic salts with alkali, alkaline earth metal or the like such as salts with sodium, potassium, triethylamine, etc., and further means esterified carboxyl group. Examples of these esters include methyl, ethyl, tert-butyl, tert-amyl, benzyl, p-nitrobenzyl, alkanoyloxymethyl (acetoxymethyl, etc.), di- or tri-alkyl-silyl(trimethylsilyl, etc.), alkoxysilyl, benzhydryl, 1-indanyl, phthalidyl, 5-indanyl, phenacyl, phenyl, p-nitrophenyl, alkoxyalkyl (methoxymethyl, ethoxymethyl, etc.), alkenyl, trichloroethyl, methylsulfonylethyl, benzyloxymethyl, tert-butyl, methoxybenzyl, trityl, methylthiomethyl, pivaloyloxymethyl, α-acyloxy-α-substituted methyl such as α-acetoxybutyl, α-ethoxycarbonyloxy-α-methylmethyl, etc.-ester. These esters are desirably those which can be led to free form under such mild conditions as causing no opening of β-lactam ring. For example, use is made of such esters wherein $R_4$ can be converted to hydrogen under mild acid or alkaline conditions, e.g. diphenylmethyl, substituted phenyl, lower alkylsulfonylethyl, pivaloyloxymethyl, etc., or groups which can be eliminated by means of oxidation or reduction reaction, such as trichloroethyl group, benzyl group, etc. And, $-COOR_4$ includes such groups as

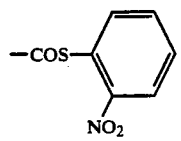

which can be readily hydrolyzed to convert into $-COOH$.

The compound (VIII) is subjected to acylation in the free state, or as a salt formed at the carboxyl group with an alkali or alkaline earth metal such as sodium, potassium or calcium, etc. or with an organic amine such as trimethylamine, pyridine, etc., or as a reactive derivative such as an acid halide (e.g. acid chloride, acid bromide), an acid anhydride, a mixed acid anhydride, an active amide, an active ester, etc. As the active ester, use is made of, for example, p-nitrophenylester, 2,4-dinitrophenylester, pentachlorophenylester, N-hydroxysuccinoimidoester or N-hydroxyphthalimidoester, etc. As the mixed acid anhydride, use is made of, for example, a mixed acid anhydride with a carbonic acid monoester such as monomethyl carbonate, monoisobutyl carbonate, or a mixed acid anhydride with a lower alkanoic acid optionally substituted with a halogen such as pyvalic acid or trichloroacetic acid, etc. When the compound (VIII) is used in the state of free acid or a salt, a suitable condensing agent is used. Examples of the condensing agent include N,N,-di-substituted carbodiimides such as N,N-dicyclohexylcarbodimide, azolide compounds such as N,N'-carbonyldiimidazole, N,N'-thionyldiimidazole, a dehydrating agent such as N-ethoxycarbonyl-2-ethoxy-1,2-dihydroquinoline, phosphorus oxychloride, alkoxyacetylene, etc., 2-halogeno-pyridinium salts (e.g. 2-chloropyridiniummethyliodide, 2-fluoropyridiniummethyliodide), etc. When such a condensing agent as above is used, it is considered that the reaction proceeds via a reactive derivative of the compound (VIII). The reaction is usually conducted in a suitable solvent. As the solvent, use is often made of halogenated hydrocarbon such as chloroform, methylene chloride, etc., ethers such as tetrahydrofuran, dioxane, etc., dimethylformamide, dimethylacetamide, acetone, water, etc. or a mixture of them. The amount of the compound (VIII) or its reactive derivative is usually about 1 to several mol. relative to 1 mol. of the compound (IX). The reaction temperature is generally in the range of from $-50°$ C. to $40°$ C. The reaction time ranges usually from 10 minutes to 48 hours, preferably 30 minutes to 10 hours. The thus-obtained compound (X) can be isolated by a conventional means, but it is used as the starting material for the subsequent process. Leading of the compound (VIII) to its salt or a reactive derivative can be conducted by a per se known means to persons having ordinary skill in the art.

The process ⑦ comprises allowing the compound (X) thus produced or a salt thereof to react with thiourea to obtain the compound (XI) or a salt thereof. This reaction is carried out usually in a solvent. As the solvent, use is made of any one which does not hamper the reaction, as exemplified by water, methanol, ethanol, acetone, tetrahydrofuran, dioxane, N,N-dimethylformamide, N,N-dimethylacetamide, N-methylpiperidone, etc. or a mixture of them. The reaction is carried out under ice-cooling, at room temperature or under heating ($-30°$ C. to $80°$ C.). The amount of the compound (XI) usually ranges from one to several equivalents relative to the compound (X), and the reaction time ranges from 1 to 48 hours, preferably 1 to 10 hours. The thus-obtained compound (XI) can be isolated and purified by conventional means such as concentration, concentration under reduced pressure, crystallization, recrystallization, solvent extraction, pH change, salting out, fractional distillation, distillation, chromatography, etc. The compounds shown by (V), (VI), (VII), (VIII), (X) and (XI) may be either syn-isomers or anti-isomers or a mixture of them. Both syn-isomers and anti-isomers are useful, but, in the compound (XI), syn-isomers are stronger than anti-isomers in antimicrobial activity, and, therefore, in the compounds of (V), (VI), (VII), (VIII), (X) and (XI), syn-isomers are preferable.

As compared with conventional methods of producing tert-butyl 3-oxobutyrate, the method of this invention is excellent in, among others, the following respects:

(1) the reaction proceeds under mild conditions,
(2) the reaction can be allowed to proceed advantageously without using solvent,
(3) the reaction mixture is not colored,
(4) therefore, no decolorizing refining process is required for obtaining a colorless product, and the reaction mixture itself can be used as the starting material for the subsequent process, and
(5) the object product can be obtained in a high purity and in a high yield.

Thus, the method of this invention is remarkably advantageous for industrial production of tert-butyl 3-oxobutyrate. Consequently, in the industrial production of the final object product using tert-butyl 3-oxobutyrate as the synthetic intermediate, the method of this invention can be an advantageous one for producing the said synthetic intermediate. For example, according to the method of this invention, as described in detail in the foregoing, an aminothiazole type cephalosporin compound (XI) and salts thereof having excellent antimicrobial activity can be produced with an industrial advantage.

The following Working Examples are given below to illustrate the present invention in more detail, but these are not intended to limit the present invention in any way.

Symbols used in the Working Examples have the following significances.

s: singlet, $CDCl_3$: deuteriochloroform, %: weight NMR (nuclear magnetic resonance spectrum): unless otherwise specified, measured by using tetramethylsilane as the internal standard at 90 MHz, and showing the values of chemical shift with $\delta$(ppm).

WORKING EXAMPLE 1

To a mixture of tert-butyl alcohol [74.1 g] and 4-(dimethylamino)pyridine [0.61 g] was added dropwise diketene [84.1 g] at 50° to 60° C. in the course of one hour while stirring. The stirring was continued for one further hour at 30° to 50° C. to obtain a colorless and clear reaction mixture, which was subjected to distillation under reduced pressure (b.p. 85° C./20 mmHg) to yield tert-butyl 3-oxobutyrate [156 g] as an oily product. The yield was 98.6%. NMR($CDCl_3$): $\delta$3.34(2H,s), 2.25(3H,s), 1.47(9H,s)ppm.

WORKING EXAMPLE 2

(Method of preparing tert-butyl 2-methoxyimino-3-oxobutyrate)

To a mixture of tert-butyl alcohol [741.2 g] and 4-(dimethylamino)pyridine [6.1 g] was added dropwise diketene [840.7 g] at 50° to 60° C. in the course of one hour while stirring. The stirring was continued for one further hour at 30° to 50° C. To the colorless and clear reaction mixture thus obtained was added acetic acid [1501 g]. To the resultant solution was added dropwise a solution of sodium nitrite [773.2 g] in water [1.35 l] at 5° to 9° C. in the course of 1.5 hour, followed by stirring for 1.5 hour at 8° to 18° C. To the reaction mixture were added toluene [1.42 l] and a 5% aqueous solution of sodium chloride [1.3 l], to which was then added sodium hydroxide [600 g] in water [1.1 l] to render the pH to 6.7. The reaction mixture was separated into two layers, and the aqueous layer was subjected to extraction with toluene (0.7 l). The extract was combined with the toluene layer and washed with a 5% aqueous solution of sodium chloride (1.2 l), from which toluene was distilled off under reduced pressure to leave crude product of tert-butyl 2-hydroxyimino-3-oxobutyrate as a viscous oily substance.

To the tert-butyl 2-hydroxyimino-3-oxobutyrate was added water [6 l], to which was added 30% sodium hydroxide [800 ml] at 28° C. while stirring to render the pH to 9.0. To the resultant solution was added dimethyl sulfate [1324 g] at 28° to 30° C. in the course of 20 minutes, which was stirred for 4 hours while adding thereto at 25° to 30° C. a 30% aqueous solution of sodium hydroxide [500 ml] to adjust the pH within the range of 8.7 to 9.0. After completion of the reaction, extraction was conducted with methylene chloride [4 l], and the aqueous layer was subjected to further extraction with methylene chloride [2 l]. The methylene chloride layers were combined and washed with a 1N aqueous solution of sodium hydroxide, 1N HCl, a 5% aqueous solution of sodium hydrogencarbonate and water, each one litre portion, successively. The resultant solution was dried over anhydrous sodium sulfate [700 g], followed by concentration under reduced pressure to obtain tert-butyl 2-methoxyimino-3-oxobutyrate [1878 g] as an oily product. The yield was 93.3%. NMR($CDCl_3$): $\delta$4.08 (3H,s), 2.36(3H,s), 1.53(9H,s)ppm.

WORKING EXAMPLE 3

(1) In methylene chloride [2.8 l] was dissolved tert-butyl 2-methoxyimino-3-oxobutyrate [805 g] obtained in Working Example 2. Into this solution was introduced hydrogen chloride [210 g] by blowing at 3° to 6° C. in the course of 8 hours, followed by leaving the system standing for 15 hours at 5° C. The supernatant was concentrated to dryness to obtain 2-methoxyimino-3-oxobutyrate [556 g] as a crystalline solid matter. The yield was 95.8%. NMR($CDCl_3$): $\delta$4.17(3H,s), 2.44(3H,s) ppm. (2) In methylene chloride [3 l] was dissolved 2-methoxyimino-3-oxobutyric acid [460 g] obtained in the above operation (1). To the solution was added a 25% solution of hydrogen bromide in acetic acid [46 ml]. To this solution was added dropwise at 7° to 15° C. a solution of bromine [372 g] in methylene chloride [372 ml] in the course of 2 hours. Then, nitrogen was vigorously blown into the system for 30 minutes at 7° to 8° C. to eliminate hydrogen bromide which formed as the by-product. To the supernatant were added silica gel (Kieselguhr 60, 70 to 230 mesh, manufactured by Merck) [80 g] and activated charcoal (Shiragi coarse particles, manufactured by Takeda Chemical Industries, Ltd.) [30 g]. The mixture was stirred at 10° to 15° C. for 30 minutes, followed by filtration to remove insolubles. The filtrate was concentrated under reduced pressure, and the residual oily substance was dissolved in xylene [685 ml], which was left standing at 5° C. for 15 hours. Precipitating crystals were collected by filtration, and the crystals were washed with a mixture of xylene and n-hexane [1:1(V/V)] [100 ml] and n-hexane [200 ml], followed by drying under reduced pressure to obtain 4-bromo-2-methoxyimino-3-oxobutyric acid [434 g]. The filtrate was concentrated under reduced pressure. To the residual oily substance was added a mixture of xylene and n-hexane [100:15 (V/V)] [238 ml] to cause crystallization to obtain further 4-bromo-2-methoxyimino-3-oxobutyric acid [82.3 g]. The yield was 72.7%.

NMR(CDCl₃): δ4.36(2H,s), 4.20(3H,s), ppm (3) To methylene chloride [50 ml] was added phosphorus pentachloride [2.62 g], and the mixture was stirred, to which was added, while cooling at 0° to 5° C., 4-bromo-2-methoxyimino-3-oxo-butyric acid [2.06 g] obtained in the above (2). The mixture was stirred at the same temperature range for one hour. To the reaction mixture was added water [25 ml], which was stirred, followed by separating into two layers. The organic layer was washed with water [5 ml] and subjected to distillation under reduced pressure to remove the solvent. The residue was dissolved in tetrahydrofuran [5 ml] to give a solution of 4-bromo-2-methoxyimino-3-oxobutyryl chloride.

(4) In a mixture solvent of water [12 ml] and tetrahydrofuran [7 ml] were dissolved 7β-amino-3-(1,2,3-thiadiazole-5-yl)thiomethyl-3-cephem-4-carboxylic acid [1.65 g] and sodium hydrogencarbonate [1.68 g]. To the solution was added the solution of 4-bromo-2-methoxyimino-3-oxobutyryl chloride obtained in the above (3). The mixture was stirred at 20° to 25° C. for 5 minutes to allow 7β-[4-bromo-2-methoxyimino-3-oxobutylamido]-3-(1,2,3-thiadiazol-5-yl)thiomethyl-3-cephem-4-carboxylic acid to be produced in the reaction mixture. To the reaction mixture was then added a solution of thiourea [1.52 g] dissolved in a mixture of water [3 ml] and tetrahydrofuran [3 ml], and the whole mixture was stirred for one hour at the same temperature range. To the resultant mixture was added sodium chloride [3.7 g], which was stirred for three hours at 5° to 10° C. Precipitating solid matter was collected by filtration and washed with tetrahydrofuran [15 ml], followed by drying under reduced pressure to afford sodium salt of 7β-[2-(2-aminothiazol-4-yl)-(Z)-2-methoxyiminoacetamido]-3-(1,2,3-thiadiazol-5-yl)thiomethyl-3-cephem-4-carboxylic acid [2.35 g]. The yield was 87.9%.

COMPARATIVE EXAMPLE

[Method described in Organic Synthesis, 42, pp.28 to 29 (1962)]

To tert-butyl alcohol [79 g (1.07 mol.)] heated at 80° to 85° C. was added, while stirring, anhydrous sodium acetate [0.4 g (4.8 mmol.)]. To the mixture was then added dropwise diketene [96 g (1.14 mol.)] in the course of 2.5 hours. During the initial 15 minutes, the addition was carried out at 60° to 70° C., then while heating up to 110° to 115° C. After the dropwise addition of diketene, the resulting blackish brown reaction mixture was stirred for further 30 minutes, immediately followed by distillation under reduced pressure to afford tert-butyl 3-oxobutyrate, b.p. 85° C./20mmHg. The yield was 135 g (80%).

(1) The reaction mixture obtained by the known method in this Comparative Example is, as apparent from the above, colored blackish brown. Therefore, in order to obtain a colorless product from the above-mentioned reaction mixture, a decolorizing purification process is inevitably necessary. On the other hand, the reaction mixture of tert-butyl 3-oxo-butyrate obtained by the method of this invention is colorless and clear, as apparent from the above Working Examples 1 and 2, and no decolorizing purification process is required. Accordingly, it is apparent that the method of this invention for preparing tert-butyl 3-oxobutyrate is remarkably superior to conventional methods from an industrial viewpoint, because the process of decolorizing purification of the reaction mixture can be saved.

(2) The yield (weight %) of the product obtained by the method of the present invention was, as apparent from Working Example 1, 98.6%, while that of the product obtained by the conventional method in the above Comparative Example was 80%, i.e. the former being higher than the latter by about 19%. Therefore, the method of the present invention is superior to conventional ones in respect of the yield as well.

What we claim is:

1. A method of producing a cephalosporin compound of the formula:

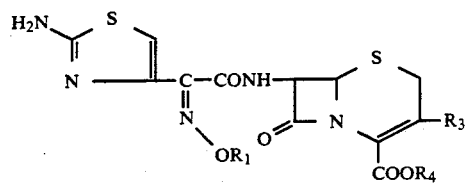

wherein R₁ stands for a C₁₋₄ alkyl group optionally substituted with carboxyl or a C₁₋₄ alkoxy-carbonyl group, R₃ stands for hydrogen atom or a standard cephalosporin substituent and R₄ stands for hydrogen atom or a group which can be converted to hydrogen under mild acid or alkaline conditions or eliminated by means of oxidation or reduction, or a salt thereof, which is characterized by allowing tert-butyl alcohol to react with diketene in the presence of 4-(tertiary amino)pyridine to give tert-butyl 3-oxobutyrate, by allowing the tert-butyl 3-oxobutyrate to react with a nitrosating agent to give tert-butyl 2-hydroxyimino-3-oxobutyrate or a salt thereof, by subjecting the tert-butyl 2-hydroxyimino-3-oxobutyrate or salt thereof to alkylation to give tert-butyl 2-alkoxyimino-3-oxobutyrate, by subjecting the tert-butyl 2-alkoxyimino-3-oxobutyrate to de-esterification to give 2-alkoxyimino-3-oxobutyric acid, by subjecting the 2-alkoxyimino-3-oxobutyric acid to halogenation to give 4-halogeno-2-alkoxyimino-3-oxobutyric acid, by allowing thus produced 4-halogeno-2-alkoxyimino-3-oxobutyric acid or a salt thereof or a reactive derivative thereof to react with a 7-aminocephalosporanic acid compound represented by the formula:

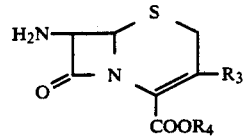

wherein R₃ and R₄ are of the same meaning defined as above, or a salt thereof to give a compound represented by the formula:

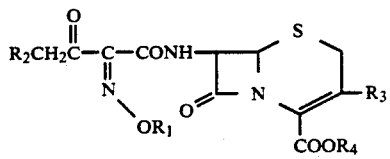

wherein R₂ stands for a halogen atom, and R₁, R₃ and R₄ are of the same meaning defined as above, or a salt thereof, followed by allowing the said compound or salt to react with thiourea.

2. A method according to claim 1, wherein the 4-(tertiary amino)pyridine is a compound of the formula:

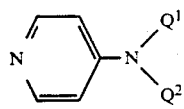

wherein $Q^1$ and $Q^2$ independently stand for a $C_{1-6}$ alkyl group or combinedly together with the adjacent nitrogen atom form a cyclic amino group.

3. A method according to claim 1, wherein the cyclic amino group is piperidino, 4-methyl piperidino or pyrrolidino.

4. A method according to claim 1, wherein the 4-(tertiary amino)pyridine is a 4-(di-$C_{1-3}$ alkylamino)-pyridine.

5. A method according to claim 1, wherein the reaction is carried out by adding diketene dropwise to a mixture of tert-butyl alcohol and 4-(tertiary amino)pyridine 6. A method according to claim 1, wherein $R_1$ is a $C_{1-4}$ alkyl group.

7. A method according to claim 1, wherein $R_3$ is hydrogen atom; —$CH_2R_5$ wherein $R_5$ is hydrogen atom, hydroxyl group, mercapto group, a lower aliphatic acyloxy group having 2 to 4 carbon atoms optionally substituted by oxo, carboxyl or $C_{1-4}$ alkoxycarbamoyl, an aromatic acyloxy group optionally substituted by hydroxyl, carboxyl, $C_{1-4}$ alkoxycarbonylcarbamoyl or $C_{1-4}$ alkoxycarbonylsulfamoyl, carbamoyloxy, cyano, azido, amino, carbamoyloxy, cyano, azido, amino, carbamoylthio, thiocarbamoyloxy, carbamoyloxy wherein the amino group is protected with the conventional protective group for amino, phenylglycyloxy, these residual groups of nucleophilic compounds substituted with $C_{1-3}$ alkyl, $C_{2-4}$ aliphatic acyl or aromatic acyl, a quaternary ammonium, or a heterocyclic thio group having a 5- or 6-membered ring containing 1 to 4 hetero-atoms selected from the group consisting of O, S and N wherein the nitrogen is optionally in the form of oxide and the heterocyclic ring is optionally substituted with one or two groups selected from $C_{1-3}$ alkyl, $C_{1-3}$ alkoxy, halogen, trihalogeno-substituted $C_{1-3}$ alkyl, hydroxyl, mercapto, amino, carboxyl, carbamoyl, di-$C_{1-3}$ alkylamino-$C_{1-3}$ alkyl and carboxymethyl groups; halogen atom; hydroxyl, $C_{2-4}$ alkenyl, thiol or amino optionally substituted with a substituent selected from the group consisting of $C_{1-4}$ alkyl, $C_{7-9}$ aralkyl, $C_{6-10}$ aryl and $C_{2-8}$ acyl, the substituent being optionally substituted with carboxyl, sulfo or hydroxyl group, wherein the substituted amino group may form pyrrolidino, morpholino or thiomorpholino together with the N-atom; or

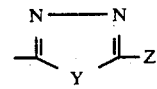

wherein Y is oxygen atom, sulfur atom or an imino group optionally substituted with a $C_{1-3}$ alkyl, $C_{1-4}$ alkyl substituted with hydroxyl, mercapto, amino morpholino, carboxyl, sulfo, carbamoyl, $C_{2-6}$ alkoxycarbonyl, $C_{2-6}$ alkylcarbamoyl, $C_{1-4}$ alkoxy, $C_{1-4}$ alkylthio, $C_{1-4}$ alkylsulfonyl, $C_{2-4}$ acyloxy or morpholinocarbonyl, $C_{6-10}$ aryl, $C_{7-10}$ aralkyl, or $C_{1-5}$ acyl; and Z is hydrogen atom or hydroxyl, amino, thiol, $C_{1-3}$ alkyl, $C_{7-10}$ aralkyl or $C_{6-10}$ aryl group optionally substituted with a substituent selected from the group consisting of $C_{1-3}$ alkyl, $C_{1-5}$ acyl, $C_{7-10}$ aralkyl and $C_{6-10}$ aryl, the substituent being optionally substituted with carboxyl, sulfo or hydroxyl, wherein the substituted amino may for pyrrolidino, morpholino or thiomorpholino together with the N-atom.

8. A method according to claim 1, wherein $R_3$ is thiadiazolylthiomethyl.

9. A method according to claim 1, wherein 7β-[2-(2-aminothiazol-4-yl)-(Z)-2-methoxyiminoacetamido]3-(1,2,3-thiadiazol-5-yl)thiomethyl-3-cephem-4-carboxylic acid is produced.

* * * * *

UNITED STATES PATENT AND TRADEMARK OFFICE
CERTIFICATE OF CORRECTION

PATENT NO. : 5,109,131
DATED : April 28, 1992
INVENTOR(S) : Kenzo NAITO et al.

It is certified that error appears in the above-identified patent and that said Letters Patent is hereby corrected as shown below:

Column 15, line 14, claim 3, line 1, change "claim 1" to --claim 2--.

Signed and Sealed this

Twenty-fourth Day of August, 1993

Attest:

BRUCE LEHMAN

*Attesting Officer*      *Commissioner of Patents and Trademarks*